United States Patent [19]
Schwartz

[11] 3,975,344

[45] Aug. 17, 1976

[54] INTERFERON PURIFICATION

[75] Inventor: Alan Asher Schwartz, Winnetka, Ill.

[73] Assignee: G. D. Searle & Co., Chicago, Ill.

[22] Filed: Oct. 2, 1974

[21] Appl. No.: 511,451

[52] U.S. Cl. .............................. 260/112 R; 424/85
[51] Int. Cl.² ..................... A61K 45/02; C07G 7/00
[58] Field of Search ................... 424/85; 260/112 R

[56] References Cited
OTHER PUBLICATIONS

Wolstenholme et al., Interferon (1967) Ciba Symposium–Little Brown Co., Boston, pp. 79 & 84.

Primary Examiner—Sam Rosen
Attorney, Agent, or Firm—Elliot N. Schubert; John J. McDonnell

[57] ABSTRACT

Interferon and interferon-like proteins isolated from animal cells are purified by means of zonal density gradient centrifugation.

8 Claims, No Drawings

INTERFERON PURIFICATION

The present invention relates to the purification of interferon or interferon-like proteins isolated from animal cells by means of zonal density gradient centrifugation.

The term interferon is intended to comprehend the substance known in the art as interferon, as described in U.S. Pat. No. 3,699,222, and also related interferon-like proteins isolated from animal cells, which substances possess the ability to combat viral-induced infections.

The protein interferon has been known for many years and is important as a natural antiviral agent. It is now possible to produce interferon in what was previously considered to be very high amounts, by suitable stimulation of cultured cells. The cells may be stimulated by a variety of agents, such as polynucleotides or viruses and much of the interferon they synthesize is released into the incubation medium. Alternatively, it is possible to produce interferon by the artificial stimulation of suitable animals with similar agents. Interferon is released into the bloodstream as a result of such stimulation and is recovered by collection of the blood. The serum may be separated from the whole blood and this serum will contain the interferon.

The interferon produced by these conventional procedures must be separated from all the reagents of the incubation medium or blood before it can be utilized as an antiviral agent. However, it is frequently found that interferon produced by the procedures above is extremely unstable during purification and consequently attempts to purify and concentrate the material using conventional protein chemistry methods result in very poor recovery of natural activity. However, it has now been found that by using the procedure of zonal density gradient centrifugation a high proportion of the initial interferon activity may be recovered, and, furthermore, that it is possible to achieve considerable enhancement of the interferon activity.

According to the present invention there is provided a method of purifying interferon in a medium containing the same, comprising subjecting said medium to the process of zonal density gradient centrifugation and collecting those fractions shown to contain interferon activity.

The material from which the interferon is purified will depend on the means by which the interferon has been obtained. When obtained by stimulation of an animal, the crude material will be contained in serum or similar blood products. Similarly, when obtained by stimulation of cell cultures, the interferon will be contained in a crude incubation medium for the cells. Alternatively, it may be preferred for technical reasons to subject the above materials to preliminary purification or concentration prior to zonal centrifugation in which case the partially purified or concentrated interferon is applied to the density gradient.

The exact conditions for the centrifugation are not critical. The procedure of zonal density gradient ultracentrifugation is preferred as large quantities of material may be treated by this procedure. The conventional conditions may be utilized in this procedure. Again, the choice of gradient material is not critical and, for example, may be cesium chloride or sucrose. The nature of the gradient and the means by which it is formed are conventional and include linear or isokinetic gradients formed statically or by prior centrifugation. The concentrated crude samples containing interferon may be applied to the gradient without further additions or may be mixed with a suitable buffer. The period of centrifugation may be determined by experimentation and will vary according to the conditions used. The purified interferon is collected from the gradient by conventional means. The fractions containing interferon are identified either by physical or chemical means, or by testing the interferon activity of all samples.

By means of the present procedure it is possible to recover considerable quantities of interferon from the culture medium or serum, depending on the source of the material. It is found that, in the case of interferon known to be unstable, the total recovery of interferon from the original sample is significantly greater than that achieved using conventional procedures. For example, the procedures of gel filtration, ion exchange or affinity chromatography are known to achieve a total recovery of between 5 and 50% when applied to interferon known to be unstable, for example human fibroblast-derived material. In contrast the practice of the present invention permits recoveries of between 50 and 100% of the total activity of similar material. In addition to the high total recovery, it is found that the interferon is purified many times compared with that present in the crude material. Clearly, the present method is advantageous in the preparation of pure interferon.

The method of the present invention will be further described by reference to the following examples. However, it is intended that these will in no way limit or define the scope of the invention.

EXAMPLE 1

Crude human interferon derived by polynucleotide induction of human fibroblasts was purified by conventional means and by zonal centrifugation. 5 Ml. of a concentrated tissue culture supernatant was applied to a 2.5 × 30 cm column of Sephadex G-100, a cross-linked dextran polymer, and eluted using a buffer of substantially neutral pH and ionic strength approximately isotonic. Fractions were collected in the conventional way and interferon recovery was determined by finding the dilution which inhibited 50% of the cytopathic effect caused by Sindbis viris on monkey kidney cell sheets. Protein recovery was determined using the method of Lowry et al. (J. Biol. Chem. 193, 265 (1951)). In a comparative experiment 20 ml. of the same concentrated tissue culture supernatant was layered onto a gradient of 5 – 20% sucrose in a Ti14 rotor in a Beckman centrifuge. The sample was centrifuged at 48,000 rpm for 41 hours at 5°C. and the fractions recovered by floating off with 30% sucrose. Protein and interferon were assayed as in the conventional purification procedure and comparative results appear in Table 1. Dramatically less interferon is lost and superior purification is achieved using the invention described.

TABLE 1

| Purification System | Interferon Yield | Interferon Purification |
|---|---|---|
| Conventional gel filtration. | 16% | × 60 |
| Zonal Centrifugation | 80% | × 200 |

EXAMPLE 2

The zonal centrifugation technique can also be applied to interferons other than human.

In this process monkey interferon with Newcastle Disease Virus was subjected to conventional and centrifugational purification procedures. The gel filtration separation system was essentially as described in the previous example, but the zonal centrifugation in this example employed a gradient of 0–25% cesium chloride and the centrifuge was run at a speed of 48,000 rpm for 48 hours at 5°C. The protein concentration was determined as before although interferon activity was measured differently, i.e. by measuring the dilution which inhibited 50% of plaques formed by vesicular stomatitis virus on monkey kidney cell sheets. Comparative results appear in Table 2. Monkey interferon is well known to be more stable to surface inactivation than human material and so the difference between methods is rather less dramatic.

TABLE 2

| Purification System | Interferon Yield | Interferon Purification |
| --- | --- | --- |
| Conventional gel filtration | 80% | 200 |
| Zonal Centrifugation | 100% | 500 |

EXAMPLE 3

Human interferon is prepared by virus induction of fresh human leucocytes (buffy coat). No attempt is made to remove the inducing virus (The conventional purification route requires extensive treatment at low pH to precipitate the virus). The crude, unconcentrated material is layered on an isokinetic sucrose gradient and centrifuged at 48,000 rpm for 41 hours. 100% of the initial activity is recovered, a 760 X purification with respect to protein is achieved, and no infectious virus or nucleic acid is present in the interferon containing fraction as measured by infectivity and chemical assay, respectively. A gel filtration experiment (essentially as outlined in Example 1) does not achieve sufficient separation between the interferon and virus to permit 100% recovery of virus-free interferon. In 3 subsequent runs on the same material the patterns of biological activity as a function of collection volume are superimposeable indicating that given constant conditions, the location of the samples of interest is predictable and need not be determined by assay.

What is claimed is:

1. A method for the purification of interferon or interferon-like proteins isolated from animal cells which comprises subjecting crude interferon or interferon-like proteins isolated from animal cells to zonal density gradient centrifugation.

2. The method of claim 1, wherein the interferon or interferon-like proteins isolated from animal cells is human interferon or interferon-like proteins isolated from animal cells.

3. The method of claim 1, wherein the interferon or interferon-like proteins isolated from animal cells is monkey interferon or interferon-like proteins isolated from animal cells.

4. The method of claim 1, wherein the gradient material is sucrose.

5. The method of claim 1, wherein the gradient material is cesium chloride.

6. The method of claim 1, wherein the interferon or interferon-like proteins isolated from animal cells is derived from human fibroblast material.

7. The method of claim 1, wherein human interferon or interferon-like proteins isolated from animal cells is purified by zonal density gradient centrifugation at 48,000 rpm for 41 hours at 5°C. and the gradient material is sucrose.

8. The method of claim 1, wherein monkey interferon or interferon-like proteins isolated from animal cells is purified by zonal density gradient centrifugation at 48,000 rpm for 48 hours at 5°C. and the gradient material is 0 – 25% cesium chloride.

* * * * *